United States Patent [19]

Tyers et al.

[11] Patent Number: 5,482,716
[45] Date of Patent: Jan. 9, 1996

[54] MEDICAMENTS

[75] Inventors: Michael B. Tyers, Welwyn; Teresa E. Challoner, Regents Park, both of England

[73] Assignee: Glaxo Group Limited, London, England

[21] Appl. No.: 250,960

[22] Filed: May 27, 1994

Related U.S. Application Data

[63] Continuation of Ser. No. 984,737, Dec. 2, 1992, abandoned, which is a continuation of Ser. No. 739,613, Aug. 2, 1991, abandoned, which is a continuation of Ser. No. 318,683, Mar. 3, 1989, abandoned.

[30] Foreign Application Priority Data

Mar. 4, 1988 [GB] United Kingdom ............. 8805269

[51] Int. Cl.$^6$ .................................................. A61F 13/00
[52] U.S. Cl. ...................... 424/422; 424/464; 424/465; 424/400
[58] Field of Search .................... 514/177, 178; 424/422, 440, 465, 464

[56] References Cited

U.S. PATENT DOCUMENTS

| | | | |
|---|---|---|---|
| 4,721,720 | 1/1988 | Tyers | 514/397 |
| 4,753,789 | 6/1988 | Tyers | 514/397 |
| 4,783,478 | 11/1988 | Tyers | 514/397 |
| 4,851,407 | 7/1989 | Tyers | 514/397 |
| 4,920,219 | 4/1990 | Pelletier | 540/523 |
| 5,166,145 | 11/1992 | Jao et al. | 514/178 |
| 5,246,709 | 9/1993 | Jao et al. | 424/465 |
| 5,310,561 | 5/1994 | Jao et al. | 424/465 |

FOREIGN PATENT DOCUMENTS

| | | |
|---|---|---|
| 201165 | 11/1986 | European Pat. Off. . |
| 226266 | 6/1987 | European Pat. Off. . |

OTHER PUBLICATIONS

Aapro et al., *New England J. of Med.*, Aug. 27, 1981, p. 520.
Aapro et al., *Cancer Treatment Reports*, 67, 11, Nov. 1983, 1013–1017.
Strum et al., *Journal of Clinical Oncology*, 2, 9, Sep. 1984, 1057–1063.
Allan et al, *British Medical Journal*, 289, Oct. 6, 1984, 878–879.
Warrington et al "Optimising antiemesis cancer therapy" Brit. Med. J. 293 1334–1337 (1986).
Smith et al "Comparison of ondansetron and ondansetron plus dexamethasone" Lancet 338 487–490 (1991).
Hawthorn & Cunningham, *Br. J. Cancer*, 1960, 61, 56–60.
Smith et al., *Br. J. Cancer*, 1990, 61, 323–324.

*Primary Examiner*—Thurman K. Page
*Assistant Examiner*—William E. Benston, Jr.
*Attorney, Agent, or Firm*—Bacon & Thomas

[57] ABSTRACT

The invention relates to the co-administration in human or veterinary medicine of 1,2,3,9-tetrahydro-9-methyl-3-[(2-methyl-1H-imidazol-1-yl)methyl]-4H-carbazol-4-one or a physiologically acceptable salt or solvate thereof and dexamethasone or a physiologically acceptable salt or ester thereof. The two active ingredients, which may be administered separately either simultaneously or sequentially, or may be combined in a single pharmaceutical preparation, are useful in the relief and/or prevention of nausea and vomiting.

13 Claims, No Drawings

MEDICAMENTS

This application is continuation of application Ser. No. 07/984,737 filed Dec. 2, 1992, now abandoned which is a continuation of application Ser. No. 07/739,613 filed Aug. 2, 1991, now abandoned; which is a continuation of application Ser. No. 07/318,683 filed Mar. 3, 1989, now abandoned.

This invention relates to improvements in the treatment of gastrointestinal disorders. More particularly it relates to the use of a compound having antagonist activity at $5HT_3$ receptors and dexamethasone in the treatment of emesis, and to pharmaceutical compositions containing the two compounds.

In our UK Patent Specification No. 2153821A we disclose inter alia 1,2,3,9-tetrahydro-9-methyl-3-[(2-methyl-1H-imidazol-1-yl)methyl]-4H-carbazol-4-one which may be represented by the formula (I)

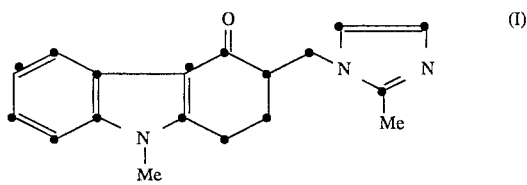

and physiologically acceptable salts, solvates and physiologically acceptable equivalents thereof.

In the aforementioned specification the compounds are described as potent and selective antagonists of 5-hydroxytryptamine (5HT) at 'neuronal' 5HT receptors of the type located on terminals of primary afferent nerves, and which are also present in the central nervous system. Receptors of this type are now designated $5HT_3$ receptors. The compounds are described as being of use in the treatment of a human or animal subject suffering from a condition caused by a disturbance of neuronal 5HT function, for example in the treatment of migraine pain or a psychotic disorder such as schizophrenia. The compounds may also be useful in the treatment of conditions such as anxiety, obesity and mania.

We have found, as described in our published European Patent Specification No. 226266, that the compounds disclosed in UK Patent Specification No. 2153821A additionally promote gastric emptying, and are thus useful in the treatment of conditions which may be relieved by the promotion of gastric emptying. Such conditions include gastric stasis and symptoms of gastrointestinal dysfunction such as dyspepais, reflux oesophagitis, peptic ulcer and flatulence.

According to published European Patent Specification No. 226266, the compounds have also been found to be anti-emetics, and may be used in the treatment or prevention of nausea and vomiting. The use of these compounds for the treatment of emesis is also described in published European Patent Specification No. 201165, which specification additionally refers to the use of the compounds for the treatment of irritable bowel syndrome.

Studies have shown that the anti-emetic properties of the compound of formula (I) are enhanced by administering the compound in conjunction with dexamethasone. Dexamethasone is a systemic anti-inflammatory corticosteroid, which is known to have anti-emetic properties and to be useful in the treatment of emesis resulting from chemotherapy, especially cancer chemotherapy involving the use of, for example, cisplatin.

The present invention thus provides a method of treating and/or preventing nausea and vomiting, which comprises administering to a human or animal subject the compound of formula (I) or a physiologically acceptable salt or solvate thereof, and dexamethasone or a physiologically acceptable salt or ester thereof.

According to another aspect the invention provides for the use of the compound of formula (I) or a physiologically acceptable salt solvate thereof for the manufacture of a medicament for administration in conjunction with dexamethasone or a physiologically acceptable salt or ester thereof, for the treatment and/or prevention of nausea and vomiting.

Co-administration of the compound of formula (I) with dexamethasone is particularly useful for the treatment and/or prevention of nausea and vomiting associated with chemotherapy, especially cancer chemotherapy involving the use of, for example, cisplatin. Such co-administration may also reduce delayed nausea and vomiting associated with this type of chemotherapy.

The compound of formula (I) or a physiologically acceptable salt or solvate thereof, and dexamethasone or a physiologically acceptable salt or ester thereof, may be administered as a single pharmaceutical composition comprising effective amounts of the two active ingredients. Alternatively the two active ingredients may be co-administered in the form of two separate pharmaceutical compositions for simultaneous or sequential use.

Suitable physiologically acceptable salts of the carbazolone of formula (I) for use according to the invention include acid addition salts formed with organic or inorganic acids for example, hydrochlorides, hydrobromides, sulphates, phosphates, citrates, fumarates and maleates. The solvates may, for example, be hydrates. A preferred form of the compound of formula (I) for use according to the invention is the hydrochloride, particularly in hydrated form, e.g. the dihydrate.

Dexamethasone may be administered according to the invention as dexamethasone alcohol or in the form of a physiologically acceptable salt or ester. Suitable salts and esters include the acetate, isonicotinoate, phenylpropionate, pivalate, t-butyl acetate, trioxaundecanoate, disodium metasulphobenzoate and disodium phosphate.

A proposed dosage of the compound of formula (I) for use according to the invention for administration to man (of approximately 70 kg body weight), is 0.05 to 25 mg, more preferably 0.05 to 20 mg, and most preferably 0.1 to 10 mg per unit dose, expressed as the weight of free base. A preferred dose of dexamethasone for use according to the invention is in the range of 0.5 to 20 mg per dosage unit, expressed as the weight of the alcohol.

The unit doses may be administered, for example, 1 to 4 times end day. The exact dose will depend on the route of administration and the condition being treated, and it will be appreciated that it may be necessary to make routine variations to the dosage depending on the age and weight of the patient as well as the severity of the condition to be treated.

When the two active ingredients are administered as separate preparations, they are preferably given orally or parenterally (e.g. intramuscularly or, more particularly, intravenously).

According to a further aspect the invention provides a pharmaceutical composition, for use in human or veterinary medicine, comprising the compound of formula (I) or a physiologically acceptable salt or solvate thereof, and dexamethasone or a physiologically acceptable salt or ester thereof.

Compositions according to the invention may be formulated in conventional manner using one or more physiologically acceptable carriers or excipients. Thus the compositions may, for example, be formulated for oral, buccal, parenteral or rectal administration. Compositions for administration by the oral route, in the form of for example tablets or capsules, are preferred.

Compositions for oral use such as tablets and capsules may be prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of one or both active ingredients.

For parenteral administration the compositions may be presented in a form suitable for bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredients may be in powder form for constitution with a suitable vehicle, e.g. sterile pyrogen-free water, before use.

For rectal administration the compositions may be formulated as suppositories or retention enemas, e.g. containing conventional suppository bases such as cocoa butter or other glycerides.

The pharmaceutical compositions of the invention may be prepared according to conventional techniques well known in the pharmaceutical industry. Thus, for example, the compound of formula (I) or a salt or solvate thereof and the dexamethasone or dexamethasone salt or ester may be admixed together, if desired, with suitable excipients. Tablets may be prepared, for example, by direct compression of such a mixture. Capsules may be prepared by filling the blend along with suitable excipients into gelatin capsules, using a suitable filling machine. Controlled release forms for oral or rectal administration may be formulated in a conventional manner associated with controlled release forms.

The compositions for use according to the invention may, if desired, be presented in a pack or dispenser device which may contain one or more unit dosage forms containing the active ingredients. The pack may for example comprise metal or plastic foil, such as a blister pack. The pack or dispenser device may be accompanied by instructions for administration. Where the compound of formula (I) and the dexamethasone are intended for administration as two separate compositions these may be presented in the form of, for example, a twin pack.

The following examples illustrate the preparation of the compound of formula (I). Temperatures are in °C.

EXAMPLE 1

1,2,3,9-Tetrahydro-9-methyl-3-[(2-methyl-1H-imidazol-1-yl)methyl]-4H-carbazol-4-one A solution of 3-[(dimethylamino)methyl]-1,2,3,9-tetrahydro-9-methyl-4H-carbazol-4-one hydrochloride (1.7 g) in water (17 ml) was treated with 2-methylimidazole (1.4 g) and then heated under reflux for 20 h. The cooled mixture was filtered and the residue washed with water (3×15 ml) to give a product (1.7 g) m.p. 221°–221.5°. This material was recrystallised from methanol to give the title compound (1.4 g) m.p. 231°–232°.

EXAMPLE 2

1,2,3,9-Tetrahydro-9-methyl-3-[(2-methyl-1H-imidazol-1-yl)methyl]-4H-carbazol-4-one hydrochloride dihydrate 1,2,3,9-Tetrahydro-9-methyl-3-[(2-methyl-1H-imidazol-1-yl)methyl]-4H-carbazol-4-one (18.3 g) in a hot mixture of isopropanol (90 ml) and water (18.3 ml) was treated with concentrated hydrochloric acid (6.25 ml). The hot mixture was filtered and the filtrate diluted with isopropanol (90 ml) and stirred at room temperature for 17 h, cooled to 2° and the solid filtered off (21.6 g.). A sample (6 g) was recrystallised from a mixture of water (6 ml) and isopropanol (10 ml) to give the title compound as a white crystalline solid (6 g) m.p. 178.5°–179.5°.

Analysis Found: C,59.45;H,6.45;N,11.5. $C_{18}H_{19}N_3O.HCl.2H_2O$ requires C,59.1;H,6.6;N,11.5%
Water assay Found: 10.23% $C_{18}H_{19}N_3O.HCl.2H_2O$ requires 9.85%

The following examples illustrate pharmaceutical compositions according to the invention, containing 1,2,3,9-tetrahydro-9-methyl-3-[(2-methyl-1H-imidazol-1-yl)methyl]-4H-carbazol-4-one hydrochloride dihydrate (Compound A) and dexamethasone as the active ingredients. Other physiologically acceptable salts and/or solvates of the compound of formula (I), and dexamethasone or physiologically acceptable salts or esters thereof, may be formulated in a similar manner.

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques.

| Direct Compression Tablets | mg/tablet | |
|---|---|---|
| Compound A | 5.0 | 10.0** |
| Dexamethasone BP | 4.0 | 4.0 |
| Anhydrous lactose USNF | 76.05 | 71.05 |
| Pregelatinised starch USNF | 4.5 | 4.50 |
| Magnesium stearate BP | 0.45 | 0.45 |
| Compression weight | 90.00 | 90.00 |

*Equivalent to 4.0 mg free base.
**Equivalent to 8.0 mg free base.

Compound A and the dexamethasone are sieved through a suitable sieve and blended with the lactose, pregelatinised starch and magnesium stearate. The resultant mix is compressed into tablets using a suitable tablet press fitted with 6.5 mm normal concave punches.

Tablets of other strengths and/or combination of doses may be prepared by appropriate alterations in the amounts of the active ingredients and the excipients and using punches to suit.

CAPSULES

|  | mg/capsule |
| --- | --- |
| Compound A | 10.00 |
| Dexamethasone BP | 4.00 |
| Pregelatinised Starch USNF | 70.625 |
| Magnesium stearate BP | 0.375 |
| Fill weight | 85.00 |

Compound A and the dexamethasone are sieved through a 250 μm sieve and blended with the pregelatinised starch and magnesium stearate. The resultant mix is filled into size 3 hard gelatin capsules using a suitable filling machine.

We claim:

1. A method for the treatment and/or prevention of nausea and vomiting which comprises administering to a human or animal subject an effective amount of 1,2,3,9-tetrahydro-9-methyl-3-[(2-methyl-1H-imidazol-1-yl)methyl]-4H-carbazol-4-one or a physiologically acceptable salt or solvate thereof in conjunction with an effective amount of dexamethasone or a physiologically acceptable salt or ester thereof.

2. A method according to claim 1 wherein said 1,2,3,9-tetrahydro-9-methyl-3-[(2-methyl-1H-imidazol-1-yl)methyl]-4H-carbazol-4-one is used in the form of a hydrochloride salt.

3. A method according to claim 2 wherein said 1,2,3,9-tetrahydro-9-methyl-3-[(2-methyl-1H-imidazol-1-yl)methyl]-4H-carbazol-4-one is used in the form of the hydrochloride dihydrate.

4. A method according to claim 1 wherein said 1,2,3,9-tetrahydro-9-methyl-3-[(2-methyl-1H-imidazol-1-yl)methyl]-4H-carbazol-4-one is administered in unit dose form of 0.05 to 25 mg per unit dose expressed as the weight of free base, and said dexamethasone is administered in unit dose form of 0.5 to 20 mg per unit dose expressed as the weight of the alcohol.

5. A method according to claim 4 in which said unit dose of 1,2,3,9-tetrahydro-9-methyl-3-[(2-methyl-1H-imidazol-1-yl)methyl]-4H-carbazol-4-one is 0.1 to 10 mg.

6. A method according to claim 1 wherein said 1,2,3,9-tetrahydro-9-methyl-3-[(2-methyl-1H-imidazol-1-yl)methyl]-4H-carbazol-4-one and said dexamethasone are administered separately.

7. A method according to claim 6 wherein said 1,2,3,9-tetrahydro-9-methyl-3-[(2-methyl-1H-imidazol-1-yl)methyl]-4H-carbazol-4-one and said dexamethasone are administered parenterally in the form of preparations adapted to be given intravenously.

8. A method for the treatment and/or prevention of nausea and vomiting which comprises administering to a human or animal subject an effective amount of 1,2,3,9-tetrahydro-9-methyl-3-[(2-methyl-1H-imidazol-1-yl)methyl]-4H-carbazol-4-one or a physiologically acceptable salt or solvate thereof in conjunction with an effective amount of dexamethasone or a physiologically acceptable salt or ester thereof, and wherein said 1,2,3,9-tetrahydro-9-methyl-3-[(2-methyl-1H-imidazol-1-yl)methyl]-4H-carbazol-4-one and said dexamethasone are administered separately and sequentially.

9. A method according to claim 8, wherein said 1,2,3,9-tetrahydro-9-methyl-3-[(2-methyl-1H-imidazol-1-yl)methyl]-4H-carbazol-4-one is used in the form of a hydrochloride salt.

10. A method according to claim 9, wherein said 1,2,3,9-tetrahydro-9-methyl-3-[(2-methyl-1H-imidazol-1-yl)methyl]-4H-carbazol-4-one is used in the form of the hydrochloride dihydrate.

11. A method according to claim 8, wherein said 1,2,3,9-tetrahydro-9-methyl-3-[(2-methyl-1H-imidazol-1-yl)methyl]-4H-carbazol-4-one is administered in unit dose form of 0.05 to 25 mg per unit dose expressed as the weight of free base, and said dexamethasone is administered as the weight of the alcohol.

12. A method according to claim 11 in which said unit dose of 1,2,3,9-tetrahydro-9-methyl-3-[(2-methyl-1H-imidazol-1-yl)methyl]-4H-carbazol-4-one is 0.1 to 10 mg.

13. A method according to claim 8 wherein said 1,2,3,9-tetrahydro-9-methyl-3-[(2-methyl-1H-imidazol-1-yl)methyl]-4H-carbazol-4-one and said dexamethasone are administered parenterally in the form of preparations adapted to be given intravenously.

* * * * *